(12) United States Patent
Singh et al.

(10) Patent No.: US 7,728,151 B2
(45) Date of Patent: Jun. 1, 2010

(54) PROCESS FOR THE PURIFICATION OF PERINDOPRIL

(75) Inventors: Girij Pal Singh, Pune (IN); Himanshu Madhav Godbole, Pune (IN); Umesh Babanrao Rananaware, Pune (IN); Vilas Nathu Dhake, Pune (IN); Suhas Ganpat Tambe, Pune (IN); Sagar Purushottam Nehate, Pune (IN)

(73) Assignee: Lupin Limited, Mumbai (IN)

( * ) Notice: Subject to any disclaimer, the term of this patent is extended or adjusted under 35 U.S.C. 154(b) by 143 days.

(21) Appl. No.: 11/886,382

(22) PCT Filed: Jun. 9, 2005

(86) PCT No.: PCT/IN2005/000189
§ 371 (c)(1),
(2), (4) Date: Sep. 14, 2007

(87) PCT Pub. No.: WO2006/097941
PCT Pub. Date: Sep. 21, 2006

(65) Prior Publication Data
US 2008/0139823 A1 Jun. 12, 2008

(30) Foreign Application Priority Data
Mar. 14, 2005 (IN) .................. 275/MUM/2005

(51) Int. Cl.
*C07D 209/42* (2006.01)
(52) U.S. Cl. ..................................... 548/492
(58) Field of Classification Search .................. 548/492
See application file for complete search history.

(56) References Cited

U.S. PATENT DOCUMENTS 7,445,296 B1 * 11/2008 Chen ..................... 301/110.5

FOREIGN PATENT DOCUMENTS

WO WO 2004/075889 A1 9/2004

OTHER PUBLICATIONS

PCT International Search Report for PCT/IN2005/000189, mailed Mar. 3, 2006.

* cited by examiner

*Primary Examiner*—Yong Chu
(74) *Attorney, Agent, or Firm*—Merchant & Gould P.C.

(57) ABSTRACT

A dicyclohexyamine salt of compound of formula I, namely perindopril, having an X-ray powder diffraction pattern with characteristic peaks (2θ): 8.462, 10.624, 18.693, 9.424, 17.272, 14.177, 19.499, 20.765, 21.409, and 14.540.

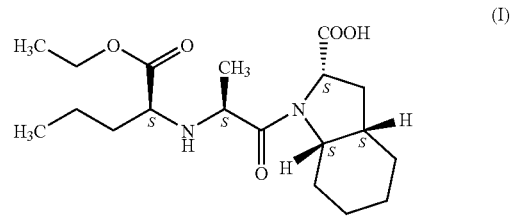

A process for preparation of the said salt of perindopril and its use in the purification of an impure perindopril and a process for purification of perindropril comprising formation of its salt with dicyclohexylamine. The present invention also relates to preparation of Perindopril tert-butyl amine salt directly from Perindopril dicyclohexylamine salt without isolating the free base.

4 Claims, 4 Drawing Sheets

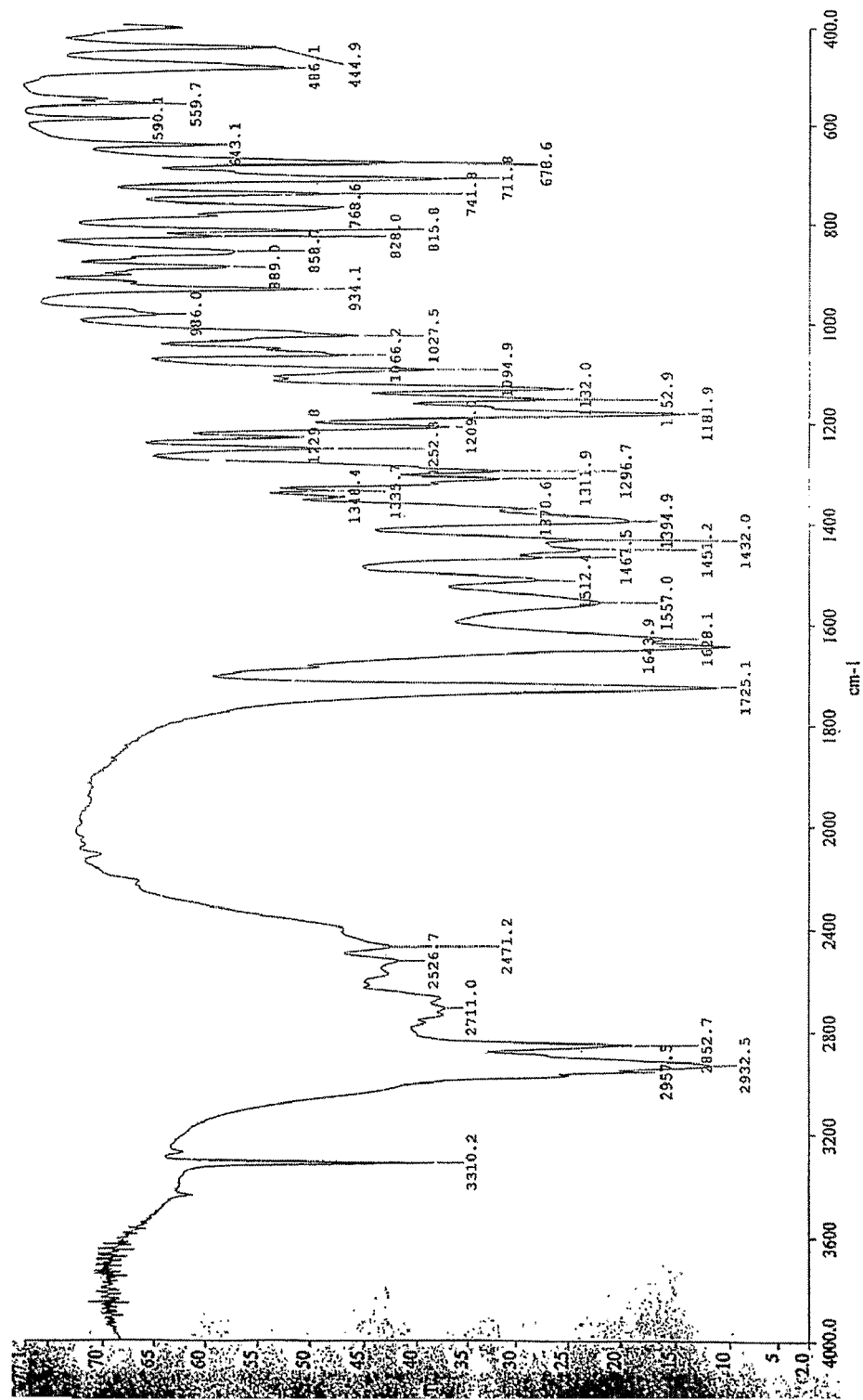
Fig. 4: The Infrared spectrum of the salt of perindopril with dicyclohexylamine.

PROCESS FOR THE PURIFICATION OF PERINDOPRIL

FIELD OF INVENTION

The present invention relates to perindopril in the form of a salt with dicyclohexylamine, a process for its production and its use in the purification of a impure perindopril and a process for purification of perindropril comprising formation of its salt with dicyclohexylamine. The present invention also relates to preparation of Perindopril tert-butyl amine salt directly from Perindopril dicyclohexylamine salt without isolating the free base.

BACKGROUND OF THE INVENTION

Perindopril(I), (2S)-2-[(1S)-1-carbethoxybutylamino]-1-oxopropyl-(2S,3aS,7aS)-perhydroindole-2-carboxylic acid of formula (I), known generically as perindopril, represented by the formula (I) is a valuable angiotensin-converting enzyme (ACE) inhibitor, a family of drugs used to treat high blood pressure and some types of heart failure.

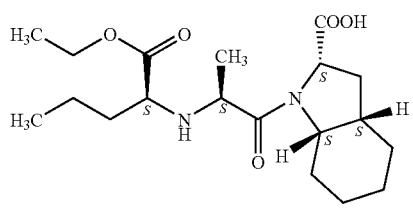
(I)

Perindopril(I) is marketed under the brandname ACEON®. It is commercially sold as the erbumine salt (II) and was launched in France in 1987; Germany in 1989; Belgium, Denmark, Ireland, Netherlands, and the UK in 1990; and in Italy in 1992 for the treatment of hypertension. This drug, which is an invention of M/S Adir et Compagnie, France is marketed by M/S Solvay Pharmaceuticals in the USA.

Perindopril is disclosed in EP 0049658 for the first time, however the synthetic procedure for preparation of perindopril was not exemplified.

European patent EP 0308341 discloses process for preparation of perindopril. According to this process the compound of the Formula V is reacted with the compound of the Formula II in the presence of dicyclohexyl carbodiimide and 1-hydroxy-benzotriazole, whereafter the benzyl ester of is debenzylated to give perindopril of the Formula I, which is then converted into the salt by reacting with t-butylamine.

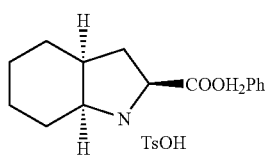
V

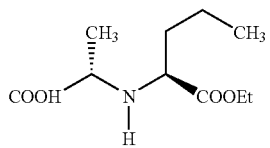
II

The drawback of this process is that the purity of the perindopril thus obtained is not satisfactory and for this reason a series of purification steps is required to provide a product which meets the severe quality requirements of pharmaceutical active ingredients. The reason of said disadvantage is that the coupling reaction of the compounds of the Formulae V and II is carried out in the presence of dicyclohexyl carbodiimide which results in the formation of a considerable amount of contaminations of the benzyl esters of the Formulae VII and VIII which are transformed by debenzylation into the compounds of the Formulae VII' and VIII'. The removal of said contaminations is cumbersome.

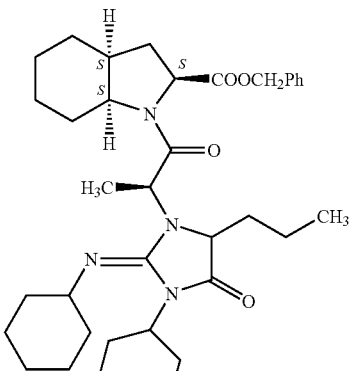
VII

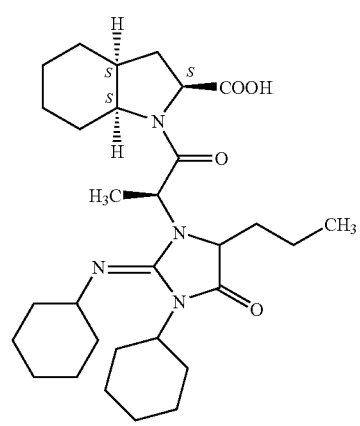
VII'

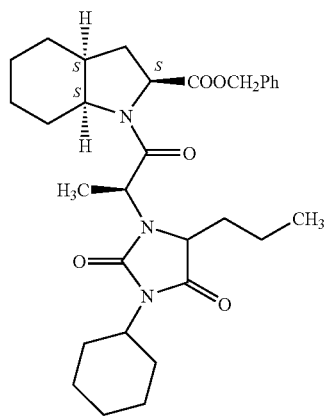
VIII

-continued

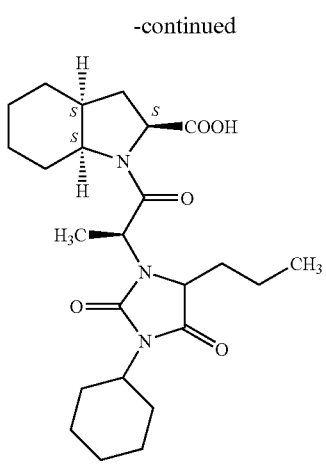

VIII'

Our copending application WO 2004/075889 teaches process for the preparation of Perindopril and salts thereof.

The process described therein comprises reaction of compound of formula A,

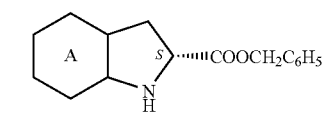

A wherein X is chlorine or bromine with compound of formula B followed by catalytic hydrogenation to give the perindopril of formula I. Converting Perindopril to tert-butyl amine salt.

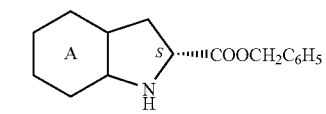

B

The Perindopril obtained from the above process contains 0.16% pharmacopoeial impurity-I (diastrereomeric impurity) of unknown nature.

Surprisingly the present inventors have found that Perindopril thus obtained when converted to dicyclohexylamine salts and then converted to its tert-butyl amine salts, all the unknown impurity found above in removed and the resulting Perindopril is more than 99.9% pure

OBJECTS OF THE INVENTION

It is therefore an object the invention to provide a process for purification of Perindopril in a mixture of a compound of formula I with impurities, without involving cumbersome process steps involving formation of contaminants which have to be further removed.

A further object of the present invention is to provide a compound of formula I in the form of a salt with dicyclohexylamine having distinct characteristics such as XRD pattern, IR spectrum, DSC, and TGA.

Another object of the invention is to provide a novel compound of formula I in the form of a salt with dicyclohexylamine which is useful in the purification of Perindopril.

Yet another object of the present invention to provide the use of a compound of formula I in the form of a salt with dicyclohexylamine, in crystalline form in the purification of a mixture of a compound of formula I with impurities.

Yet another objective is to provide a process for the preparation of more than 99.9% pure Perindopril tert-butyl amine salt.

A further objective is to provide a process for the preparation of more than 99.9% pure Perindopril tert-butyl amine salt directly from Perindopril dicyclohexylamine salt.

SUMMARY OF INVENTION

Thus according to one aspect of the present invention there is to provided a compound of formula I in the form of a salt with dicyclohexylamine having distinct characteristics such as XRD pattern, IR spectrum, DSC, and TGA According to further aspect of the present invention there is provided a process for purification of Perindopril in a mixture of a compound of formula I with impurities, said process comprising forming a salt of a compound of formula I with dicyclohexylamine; and converting the compound of formula I in the form of a salt with dicyclohexylamine, selectively in crystalline form, into a compound of formula I.

According to another aspect of present invention there is provided a process of purification of compound of formula I (Perindopril) comprising forming a salt of salt of a compound of formula I with dicyclohexylamine; and converting said dicyclohexylamine salt of compound of formula I to tert butyl amine salt of compound of formula I and isolating pure perindopril therefrom According to another aspect of the present invention there is provided a novel compound of formula I in the form of a salt with dicyclohexylamine which is useful in the purification of Perindopril.

According to another aspect of the present invention there is provided the use of a compound of formula I in the form of a salt with dicyclohexylamine, in crystalline form in the purification of a mixture of a compound of formula I with impurities.

DETAILED DESCRIPTION OF THE INVENTION

Accordingly, present invention provides an improved process for the purification of Perindopril comprising forming a salt of a compound of formula I with dicyclohexylamine and converting a compound of formula I in the form of a salt with dicyclohexylamine in crystalline form, into a compound of formula I.

In the present embodiment of the invention the purification of a compound of formula I, namely perindopril

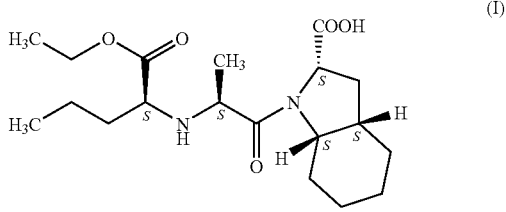

(I)

comprises steps of:
i. treating perindopril in a solvent with dicyclohexylamine to form perindopril in the form of a salt with dicyclohexylamine;
ii. isolating said dicyclohexylamine salt perindopril;
iii. treating the perindopril in the form of a salt with dicyclohexylamine with an acidic agent to form perindopril free base; and
iv. isolating perindopril free base.

The solvent utilized in the step 1 is acetonitrile and the acidic reagent utilized in step iii is HCl.

This novel crystalline form of a salt of compound of formula I, namely perindropril, with dicyclohexylamine posses distinct X-ray (powder) diffraction patterns as summarized in Table-I.

TABLE I

X-ray (powder) diffraction pattern of the crystalline dicyclohexylamine salt of perindopril

| Angle (2θ°) | d Value (A) | Intensity (%) |
|---|---|---|
| 8.462 | 10.4413 | 100.0 |
| 9.424 | 9.3771 | 8.0 |
| 10.624 | 8.3206 | 17.9 |
| 12.625 | 7.0056 | 3.5 |
| 13.268 | 6.6676 | 0.9 |
| 14.177 | 6.2419 | 6.1 |
| 14.540 | 6.0871 | 3.6 |
| 15.866 | 5.5811 | 2.5 |
| 17.272 | 5.1300 | 7.7 |
| 18.693 | 4.7431 | 11.5 |
| 19.499 | 4.5488 | 6.1 |
| 20.765 | 4.2742 | 5.6 |
| 21.409 | 4.1471 | 3.8 |
| 21.906 | 4.0542 | 2.4 |
| 23.534 | 3.7773 | 3.4 |
| 24.198 | 3.6750 | 2.3 |
| 25.040 | 3.5534 | 1.1 |
| 26.033 | 3.4200 | 1.0 |
| 26.888 | 3.3131 | 2.3 |
| 28.723 | 3.1055 | 1.1 |
| 29.966 | 2.9794 | 0.8 |
| 30.839 | 2.8971 | 1.3 |
| 32.270 | 2.7718 | 1.7 |
| 34.047 | 2.6311 | 1.1 |

In another embodiment of the present invention the process of purification of an impure compound of formula I, namely perindopril, comprises steps of:
i. treating an impure perindopril in a solvent with dicyclohexylamine to form salt of perindopril with dicyclohexylamine;
ii. isolating said dicyclohexylamine salt of a compound of formula I;
iii. treating the dicyclohexylamine salt of compound of formula I optionally in the presence of an organic solvent to form a salt with tert butyl amine.

According to another aspect there is provided a process for the purification of compound of formula I, namely Perindopril,

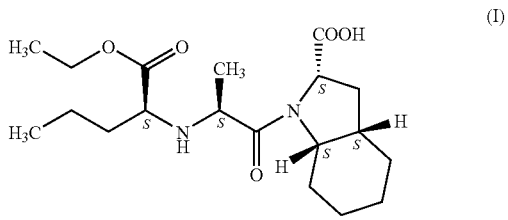

(I)

comprising steps of:
i. treating perindopril with dicyclohexylamine in the presence of a solvent to form salt of perindopril with dicyclohexylamine;
ii. isolating said dicyclohexylamine salt of a compound of formula I;
iii. treating the dicyclohexylamine salt of compound of formula I optionally in the presence of an organic solvent to form a salt with tert butyl amine;
iv. isolating compound of formula I with unknown impurities;
v. converting to dicyclohexylamine salt of compound of formula I with high purity.

The said solvent utilized in step (i) is acetonitrile. The said solvent utilized in step (iii) includes but not limited to ketones like acetone, alcohols like ethanol, nitriles like acetonitrile, nitroalkane like nitromethane, acetals such as 2,2-dimethoxy propane, ether such as diisopropyl ether, aromatic hydrocarbon like toluene, chlorinated solvents such as dichloromethane and the like or mixture thereof.

A compound of formula I in the form of a salt with dicyclohexylamine may be in a crystalline form; perindopril in the form of a salt may be obtained in surprising high purity, e.g. more than 99.9% purity; production of the salt is simple; Perindopril tert-butyl amine obtained from the Perindopril dicylohexamine salt was surprisingly pure, i.e. purity of more than 99.9%.

DESCRIPTION OF THE DRAWINGS

FIG. 4: The Infrared spectrum of the salt of perindopril with dicyclohexylamine.

Figure 1:
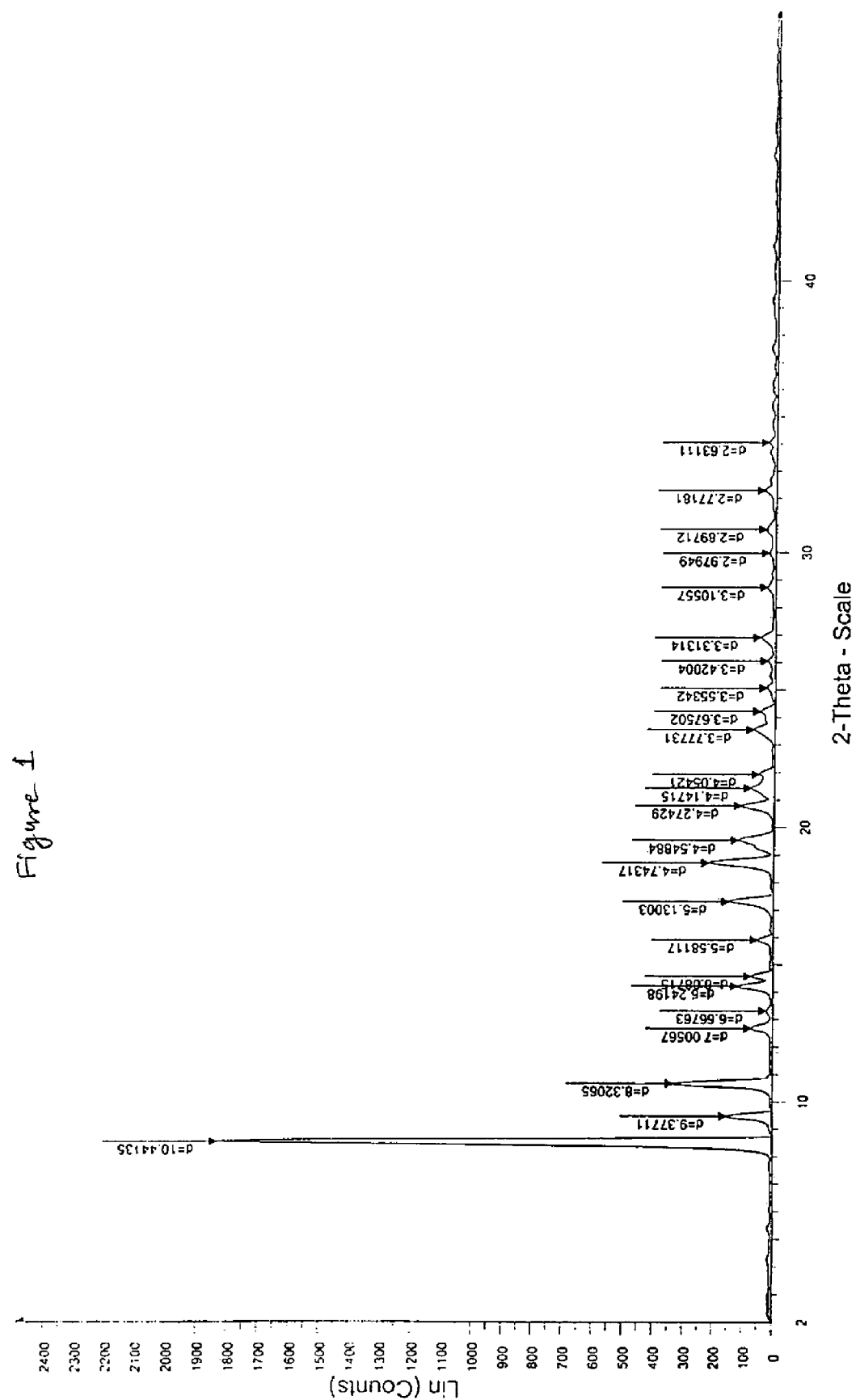
FIG. 1: The X-ray (Powder) diffraction pattern of the salt of perindopril with dicyclohexylamine.

For the purification of perindopril several other bases like arginine or acids like maleic acid, tartaric acid, oxalic acid which failed to yield the desired results.

Also, as far as the use of solvent for the preparation of dicyclohexyl amine salt is concerned it was tried to utilize several other solvents such as ketones like acetone, esters like ethyl acetate, ethers like diisopropyl ether, alcohols like ethanol, aromatic hydrocarbons like toluene or chlorinated solvents like dichloromethane failed to give a similar result.

In the following examples, which illustrate the invention without limiting the scope of the invention.

EXAMPLE 1

Preparation of Dicyclohexylamine (DCA) Salt of Perindopril

Perindopril (25 g) containing 0.16% pharmacopoeial impurity-I (diastrereomeric impurity) was taken in acetonitrile (150 ml) and stirred for about 10 minutes. The above solution was treated with dicyclohexyl amine (5.2 g) and stirred for about 8-10 hrs at room temperature. The precipitated solid was filtered and washed with acetonitrile (20 ml). The dicyclohexyl amine salt of perindopril was recrystallized in acetonitrile. Weight of dry dicyclo hexyl amine salt of perindopril was 12 g.

Melting point: 141.5° C.

IR data (cm$^{-1}$): 3310, 2932, 2852, 2711, 2526, 2471, 1725, 1628, 1643, 1557, 1512, 1451, 1394, 1311, 1296, 1209, 1181, 1152, 1132, 1094, 1066, 1027, 986, 934, 889, 828, 815, 768, 741, 711, 678, 86, 444.9.

Figure 2:
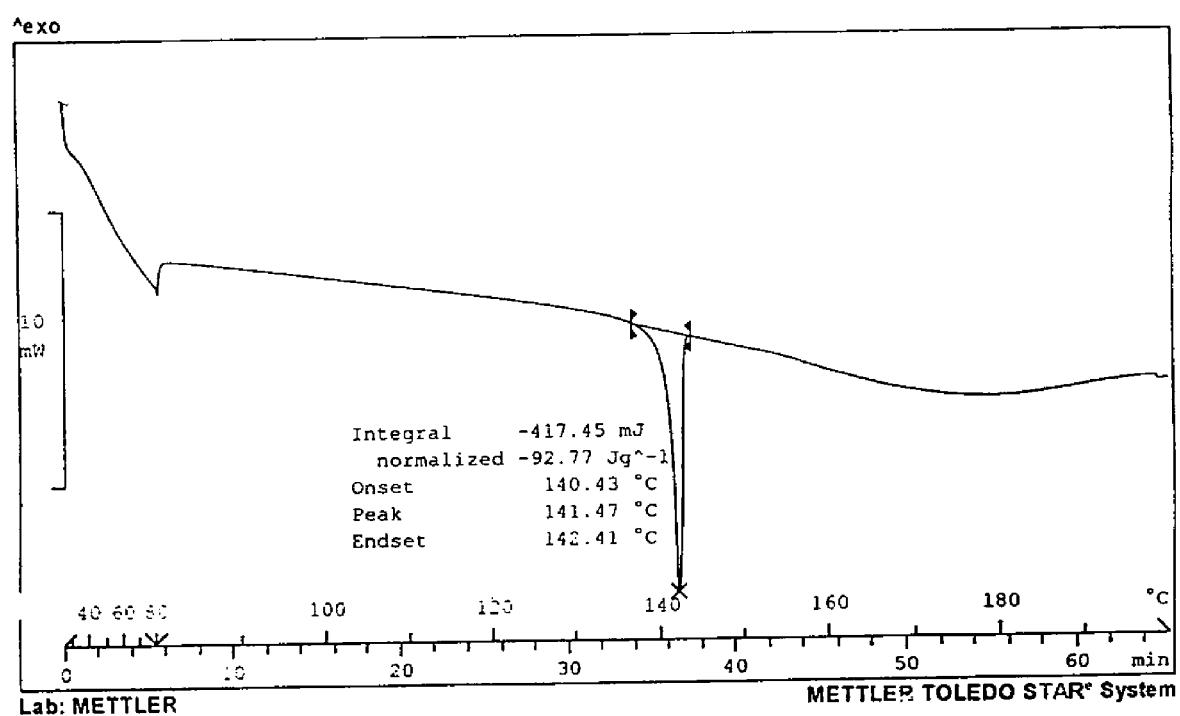
FIG. 2: The DSC thermogram of the salt of perindopril with dicyclohexylamine.
Figure 3:
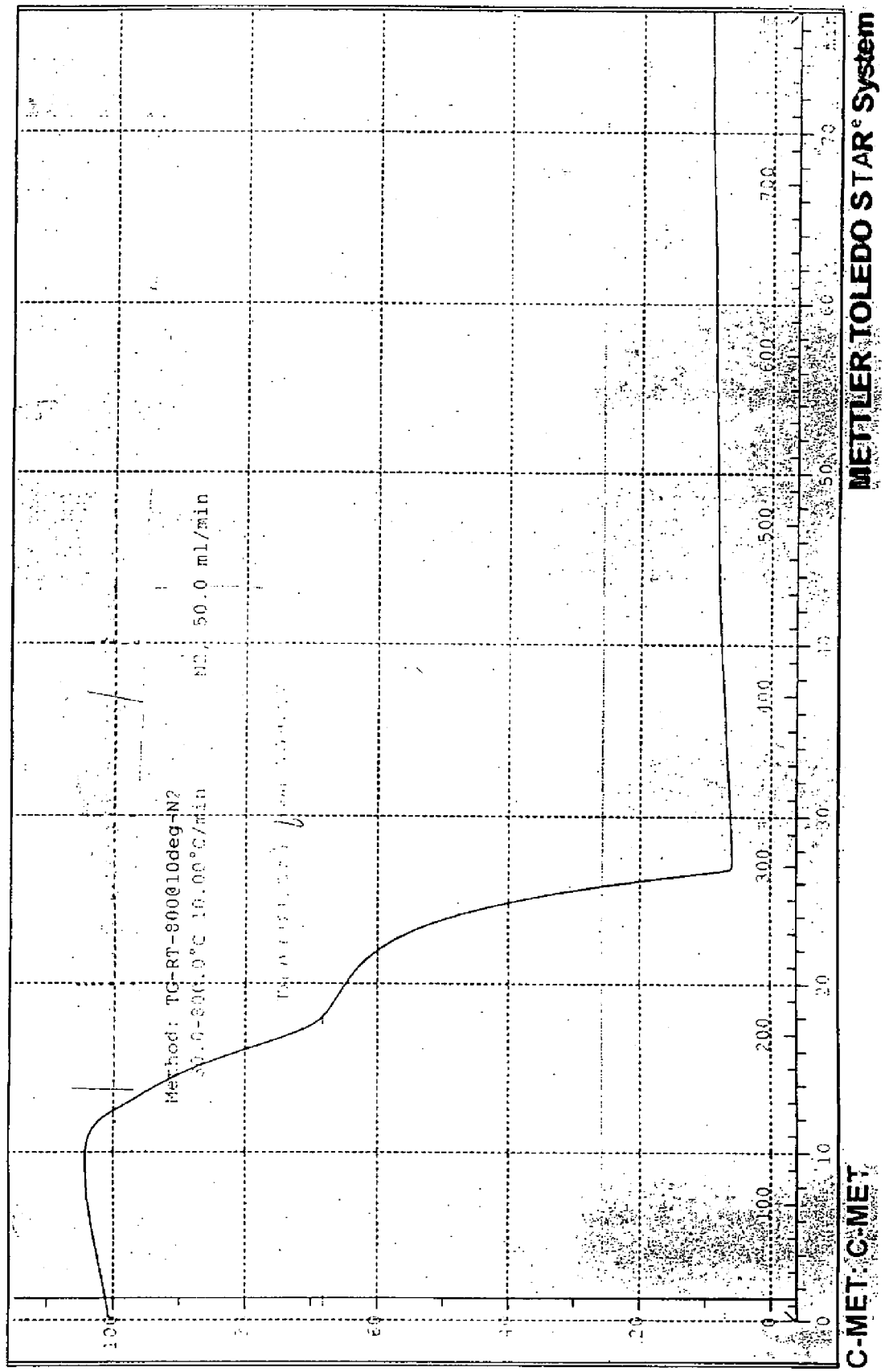
FIG. 3: The TGA thermogram of the salt of perindopril with dicyclohexylamine.

The XRD pattern, DSC, TGA as summarized in FIG. 1, FIG. 2 and FIG. 3 respectively.

EXAMPLE 2

Preparation of Perindopril Tert Butyl Amine Salt

Dicyclohexylamine (DCA) salt of perindopril (12 g) obtained in example 1 was taken in water (60 ml) and acidified till pH 4-4.5 at temperature 0-5° C. using conc. HCl. The reaction mixture was stirred for about 15 minutes. It was then filtered and the filtrate was extracted with dichloromethane (72 ml×2). The dichloromethane layer was washed with water (24 ml×2). Concentration of the organic layer under reduced pressure afforded highly pure perindopril (7 g). This perindopril was taken in 2,2 dimethoxy propane (70 ml) and treated with tert butyl amine (1.5 g) to get the salt as a white solid. The reaction mixture was subjected to a gentle reflux till a solution resulted. The solution was then cooled to 25-30° C., filtered and dried under reduced pressure. The Perindopril thus obtained is having purity of more than 99.9% by HPLC. Dry weight of Perindopril tertiary butyl amine: 6.5 g.

EXAMPLE 3

Preparation of Perindopril Tert Butyl Amine Salt

Dicyclohexyl amine salt of perindopril (10 g) obtained in example 1 was slurried in 2,2 dimethoxy propane (100 ml). To the slurry was added tertiary butyl amine (5.8 ml) at 25-30 C to afford the tertiary butyl amine salt of perindopril as a white solid. The product was collected by filtration under suction. It was dried under reduced pressure at 40-45 C. The perindopril tert butyl amine salt thus obtained is more than 99.9% pure by HPLC.

Dry weight of Perindopril tertiary butyl amine: 7.5 g.

EXAMPLE 4

Preparation of Perindopril Tert Butyl Amine Salt

Dicyclohexyl amine salt of perindopril (10 g) obtained as in example 1 was treated with tertiary butyl amine (100 ml) at 25-30 C for 4-5 hrs, when the tertiary butyl amine salt of perindopril was obtained as a white solid. The solid product was collected by filtration under suction. The solid was dried under reduced pressure at 40-45 C. The perindopril tery butyl amine salt thus obtained is having purity of more than 99.9% by HPLC.

Dry weight of Perindopril tertiary butyl amine: 6.6 g.

EXAMPLE 5

Preparation of Dicyclohexylamine (DCA) Salt of Perindopril

Perindopril (25 g) obtained by process disclosed in EP 0308341 having purity of 99.86% and containing 0.14% pharmacopoeial impurity was taken in acetonitrile (150 ml) and stirred for about 10 minutes. The above solution was treated with dicyclohexyl amine (5.2 g) and stirred for about 8-10 hrs at room temperature. The precipitated solid was filtered and washed with acetonitrile (20 ml). The dicyclohexyl amine salt of perindopril was recrystallized in acetonitrile. Weight of dry dicyclo hexyl amine salt of perindopril was 12 g.

Melting point: 141.5° C.

IR data (cm$^{-1}$): 3310, 2932, 2852, 2711, 2526, 2471, 1725, 1628, 1643, 1557, 1512, 1451, 1394, 1311, 1296, 1209, 1181, 1152, 1132, 1094, 1066, 1027, 986, 934, 889, 828, 815, 768, 741, 711, 678, 86, 444.9.

The XRD pattern, DSC, TGA as summarized in FIG. 1, FIG. 2 and FIG. 3 respectively.

EXAMPLE 6

Preparation of Perindopril Tert Butyl Amine Salt

Dicyclohexyl amine salt of perindopril (10 g) obtained as in example 5 was treated with tertiary butyl amine (100 ml) at 25-30 C for 4-5 hrs, when the tertiary butyl amine salt of perindopril was obtained as a white solid. The solid product was collected by filtration under suction. The solid was dried under reduced pressure at 40-45 C. The perindopril tery butyl amine salt thus obtained is having purity of more than 99.9% by HPLC. Dry weight of Perindopril tertiary butyl amine: 6.6 g.

EXAMPLE 7

Perindopril (25 g) containing 0.16% pharmacopoeial impurity-I (diastrereomeric impurity) was dissolved in DM water (125 ml) and the solution was cooled to 0-5 C. To the solution was added dichloromethane (125 ml) and the pH of the biphasic solution was adjusted to 4.2-4.5 using 10% hydrochloric acid. The organic layer was separated. The aqueous layer was re-extracted with dichloromethane (125 ml) and the resulting organic layer was mixed with the earlier one. Concentration of the organic layer under reduced pressure at 25-30 C afforded free perindopril as a fluffy solid (18 g). The free perindopril still contained 0.16% impurity-I.

The perindopril (15 g) was dissolved in acetonitrile (125 ml) at 25-30 C. To the solution was added dicyclohexyl amine (7.8 g) at 25-30 C. The reaction mixture was stirred at 25-30 C for 8-10 hrs, when a salt separated out. This salt was collected by filtration under suction. It was dried at 40-45 C, under reduced pressure for 8-10 hrs. This salt contained 0.04% impurity-I. Thus formation of dicyclohexyl ammine salt in acetonitrile had reduced the level of the isomeric impurity.

The dry weight of the salt was 17.5 g.

The dicyclohexyl amine salt (17 g) was further purified by crystallization in acetonitrile (170 ml), when the level of isomeric impurity-I was reduced to 0.01%. The dry weight of the recrystallized material was 16.8 g.

The dicyclohexyl amine salt of perindopril was converted into the tertiary butyl amine salt under conditions described hereinabove. The Perindopril resulting from above was surprisingly pure. The qualitative purity of perindopril tertiary butyl amine thus obtained was 99.9%, with all other impurities below 0.02%.

EXAMPLE 8

Perindopril tertiary butyl amine (25 g) containing 0.13% of an unknown impurity was dissolved in DM water (125 ml) and the solution was cooled to 0-5 C. To the solution was added dichloromethane (125 ml) and the pH of the biphasic solution was adjusted to 4.2-4.5 using 10% hydrochloric acid. The organic layer was separated. The aqueous layer was re-extracted with dichloromethane (125 ml) and the resulting organic layer was mixed with the earlier one. Concentration of the organic layer under reduced pressure at 25-30 C afforded free perindopril as a fluffy solid (18 g). The free perindopril still contained 0.13% unknown impurity.

The free perindopril (15 g) was dissolved in acetonitrile (125 ml) at 25-30 C. To the solution was added dicyclohexyl amine (7.8 g) at 25-30 C. The reaction mixture was stirred at 25-30 C for 8-10 hrs, when a salt separated out. This salt was collected by filtration under suction. It was dried at 40-45 C, under reduced pressure for 8-10 hrs. This salt contained 0.02% impurity-I. Thus formation of dicyclohexyl ammine salt in acetonitrile had substantially reduced the level of the unknown impurity. The dry weight of the salt was 17.5 g.

Use of other bases like arginine or acids like maleic acid, tartaric acid, oxalic acid failed to yield the desired results. Use of ketones like acetone, esters like ethyl acetate, ethers like diisopropyl ether, alcohols like ethanol, aromatic hydrocarbons like toluene or chlorinated solvents like dichloromethane failed to give a similar result. So also conventional crystallization of perindopril tertiary butyl amine, failed to reduce the levels of this impurity.

The invention claimed is:

1. A crystal form of a dicyclohexyamine salt of compound of formula I, namely perindopril, having an X-ray powder diffraction pattern with characteristic peaks (2θ): 8.462, 10.624, 18.693, 9.424, 17.272, 14.177, 19.499, 20.765, 21.409, and 14.540.

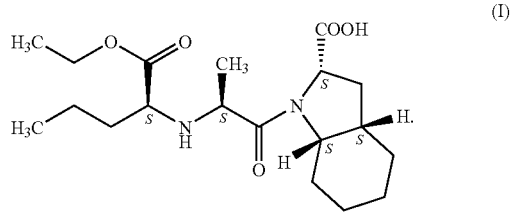

(I)

2. A crystal form of a dicyclohexyamine salt of perindopril as claimed in claim 1 having an X-ray diffractogram as set out in FIG. 1.

3. A crystal form of a dicyclohexyamine salt of perindopril as claimed in claim 1 having DSC thermogram as described in FIG. 2.

4. A crystal form of a dicyclohexyamine salt of perindopril as claimed in claim 1 having TGA thermogram as described in FIG. 3.

* * * * *